United States Patent
Chopra et al.

(10) Patent No.: US 9,227,922 B2
(45) Date of Patent: *Jan. 5, 2016

(54) AMORPHOUS AMIDES

(71) Applicant: Xerox Corporation, Norwalk, CT (US)

(72) Inventors: Naveen Chopra, Oakville (CA); Adela Goredema, Mississauga (CA); Kentaro Morimitsu, Mississauga (CA); Barkev Keoshkerian, Thornhill (CA); Jennifer L. Belelie, Oakville (CA)

(73) Assignee: Xerox Corporation, Norwalk, CT (US)

( * ) Notice: Subject to any disclaimer, the term of this patent is extended or adjusted under 35 U.S.C. 154(b) by 127 days.

This patent is subject to a terminal disclaimer.

(21) Appl. No.: 14/052,873

(22) Filed: Oct. 14, 2013

(65) Prior Publication Data

US 2015/0105587 A1 Apr. 16, 2015

(51) Int. Cl.
C07C 233/05 (2006.01)
C07C 231/08 (2006.01)

(52) U.S. Cl.
CPC ............. *C07C 233/05* (2013.01); *C07C 231/08* (2013.01); *C07C 2103/26* (2013.01)

(58) Field of Classification Search
None
See application file for complete search history.

(56) References Cited

U.S. PATENT DOCUMENTS

| | | | |
|---|---|---|---|
| 4,490,731 A | 12/1984 | Vaught | |
| 4,889,560 A | 12/1989 | Jaeger et al. | |
| 4,889,761 A | 12/1989 | Titterington et al. | |
| 5,195,430 A | 3/1993 | Rise | |
| 5,221,335 A | 6/1993 | Williams et al. | |
| 5,372,852 A | 12/1994 | Titterington et al. | |
| 5,389,958 A | 2/1995 | Bui et al. | |
| 6,547,380 B2 | 4/2003 | Smith et al. | |
| 7,973,186 B1 | 7/2011 | Goredema et al. | |
| 8,372,189 B2 | 2/2013 | Chopra et al. | |
| 8,506,040 B2 | 8/2013 | Belelie et al. | |
| 8,778,070 B1 * | 7/2014 | Chopra et al. ............ | 106/31.29 |
| 9,011,587 B1 * | 4/2015 | Goredema et al. ......... | 106/31.29 |
| 2012/0274699 A1 | 11/2012 | Belelie et al. | |
| 2013/0284056 A1 | 10/2013 | Chopra et al. | |
| 2013/0284058 A1 | 10/2013 | Morimitsu et al. | |
| 2013/0284062 A1 | 10/2013 | Morimitsu et al. | |
| 2013/0286180 A1 | 10/2013 | Iftime et al. | |

OTHER PUBLICATIONS

Chopra, et al., U.S. Appl. No. 14/052,865, filed Oct. 14, 2013, "Phase Change Ink Containing Amorphous Amides," not yet published.
Goredema, et al., U.S. Appl. No. 14/053,569, filed Oct. 14, 2013, "Novel Crystalline Compounds for Phase Change Inks," not yet published.
Goredema, et al. U.S. Appl. No. 14/053,601, filed Oct. 15, 2013, "Bio-Renewable Phase Change Inks," not yet published.
Goredema et al., U.S. Appl. No. 14/053,592, filed Oct. 14, 2013, "Phase Change Inks Comprising Novel Crystalline Compounds," not yet published.

* cited by examiner

*Primary Examiner* — Rosalynd Keys
*Assistant Examiner* — Jennifer C Sawyer
(74) *Attorney, Agent, or Firm* — Marylou J. Lavoie, Esq. LLC

(57) ABSTRACT

An amorphous amide compound of the formula

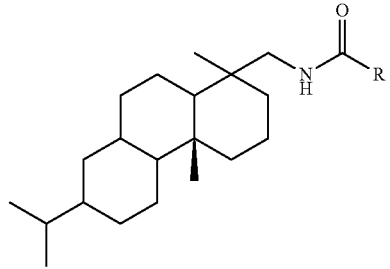

wherein R is selected from the group consisting of an alkyl group, an aryl group, an alkylaryl group, an arylalkyl group, and combinations thereof. An amorphous diamide compound of the formula

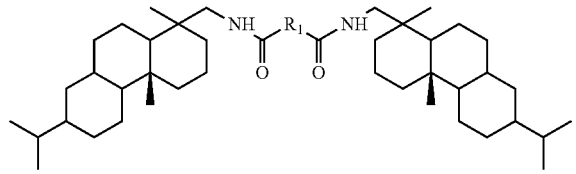

wherein $R_1$ is selected from the group consisting of an alkylene group, an arylene group, an alkylarylene group, an arylalkylene group, and combinations thereof.

11 Claims, 4 Drawing Sheets

AMORPHOUS AMIDES

RELATED APPLICATIONS

Commonly assigned U.S. patent application Ser. No. 14/052,865, entitled "Phase Change Ink Containing Amorphous Amides," having the named inventors Naveen Chopra, Adela Goredema, Kentaro Morimitsu, Barkev Keoshkerian, Jennifer L. Belelie, and Gabriel Iftime, filed concurrently herewith, is hereby incorporated by reference herein in its entirety.

Commonly assigned U.S. patent application Ser. No. 14/053,569, entitled "Novel Crystalline Compounds for Phase Change Inks," having the named inventors Adela Goredema, Jennifer Belelie, James Mayo, Daryl Vanbesien, Barkev Keoshkerian, Nathan Bamsey, and Jenny Eliyahu, filed concurrently herewith, is hereby incorporated by reference herein in its entirety.

Commonly assigned U.S. patent application Ser. No. 14/053,601, entitled "Bio-renewable Phase Change Inks," having the named inventors Adela Goredema, Jennifer Belelie, James Mayo, Daryl Vanbesien, Barkev Keoshkerian, Nathan Bamsey, and Jenny Eliyahu, filed concurrently herewith, is hereby incorporated by reference herein in its entirety.

Commonly assigned U.S. patent application Ser. No. 14/053,592, entitled "Phase Change inks Comprising Novel Crystalline Compounds," having the named inventors Adela Goredema, Guerino Sacripante, Barkev Keoshkerian, Daryl Vanbesien, Kentaro Morimitsu, Naveen Chopra, and Gabriel Iftime, filed concurrently herewith, is hereby incorporated by reference herein in its entirety.

BACKGROUND

Disclosed herein are amorphous amide compounds, particularly amorphous monoamide and amorphous bisamide compounds which are particularly suited for use in phase change ink applications.

Crystalline-amorphous inks have been described which display improved robustness over previous inks, particularly on coated substrates, and particularly with respect to scratch, fold and fold offset.

U.S. Patent Publication 2012/0274699, which is hereby incorporated by reference herein in its entirety, describes a phase change ink composition comprising an amorphous component, a crystalline component, and, optionally, a colorant.

In general, phase change inks (sometimes referred to as solid inks or "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. No. 4,889,560, U.S. Pat. No. 4,889,761, and U.S. Pat. No. 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes.

The colorants can also include pigments, as disclosed in, for example, U.S. Pat. No. 5,221,335, the disclosure of which is totally incorporated herein by reference.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

While known compositions and processes are suitable for their intended purposes, a need remains for improved materials that can provide improved thermal stability during synthesis and variation in product distributions and for composition whose synthesis can be successfully scaled up. There further remains a need for new amorphous materials that have improved properties over current materials.

The appropriate components and process aspects of the each of the foregoing U.S. Patents and Patent Publications may be selected for the present disclosure in embodiments thereof. Further, throughout this application, various publications, patents, and published patent applications are referred to by an identifying citation. The disclosures of the publications, patents, and published patent applications referenced in this application are hereby incorporated by reference into the present disclosure to more fully describe the state of the art to which this invention pertains.

SUMMARY

Described is a compound of the formula

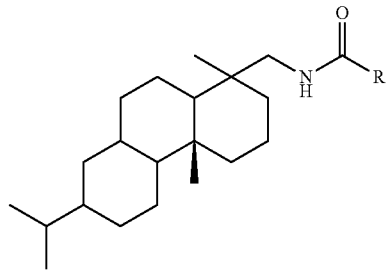

wherein R is selected from the group consisting of an alkyl group, an aryl group, an alkylaryl group, an arylalkyl group, and combinations thereof.

Also described is a compound of the formula

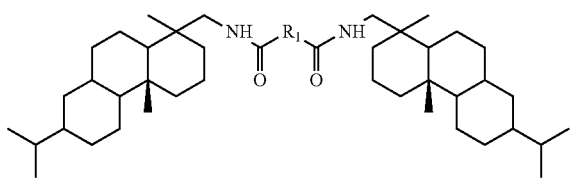

wherein $R_1$ is selected from the group consisting of an alkylene group, an arylene group, an alkylarylene group, an arylalkylene group, and combinations thereof.

Further described is a method for preparing an amorphous monoamide comprising contacting a compound of the formula

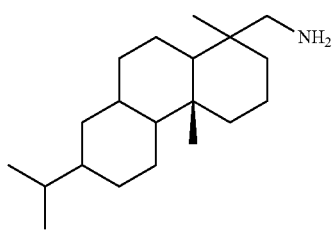 [SMILES: CC(C)C1CCC2C(CCC3C(C)(CN)CCC[C@]23C)C1]

with an acid of the formula

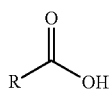

with mixing and optional heating to produce a product compound of the formula

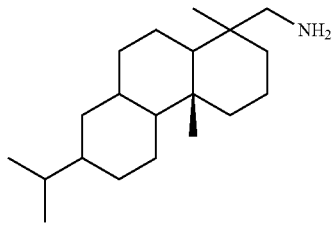

wherein R is selected from the group consisting of an alkyl group, an aryl group, an alkylaryl group, an arylalkyl group, and combinations thereof.

Further described is a method for preparing an amorphous diamide comprising contacting a compound of the formula

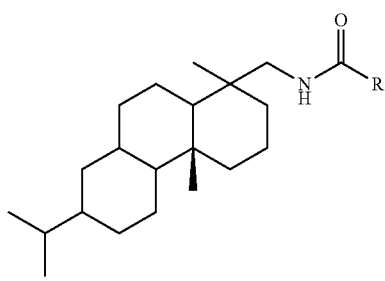

with an acid of the formula

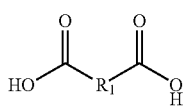

with mixing and optional heating to produce a product compound of the formula

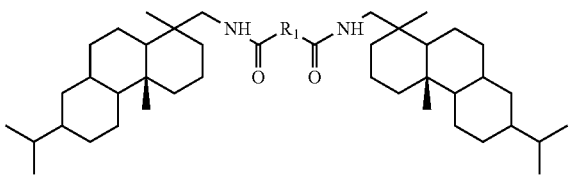

wherein $R_1$ is selected from the group consisting of an alkylene group, an arylene group, an alkylarylene group, an arylalkylene group, and combinations thereof.

DETAILED DESCRIPTION

Figure 1:
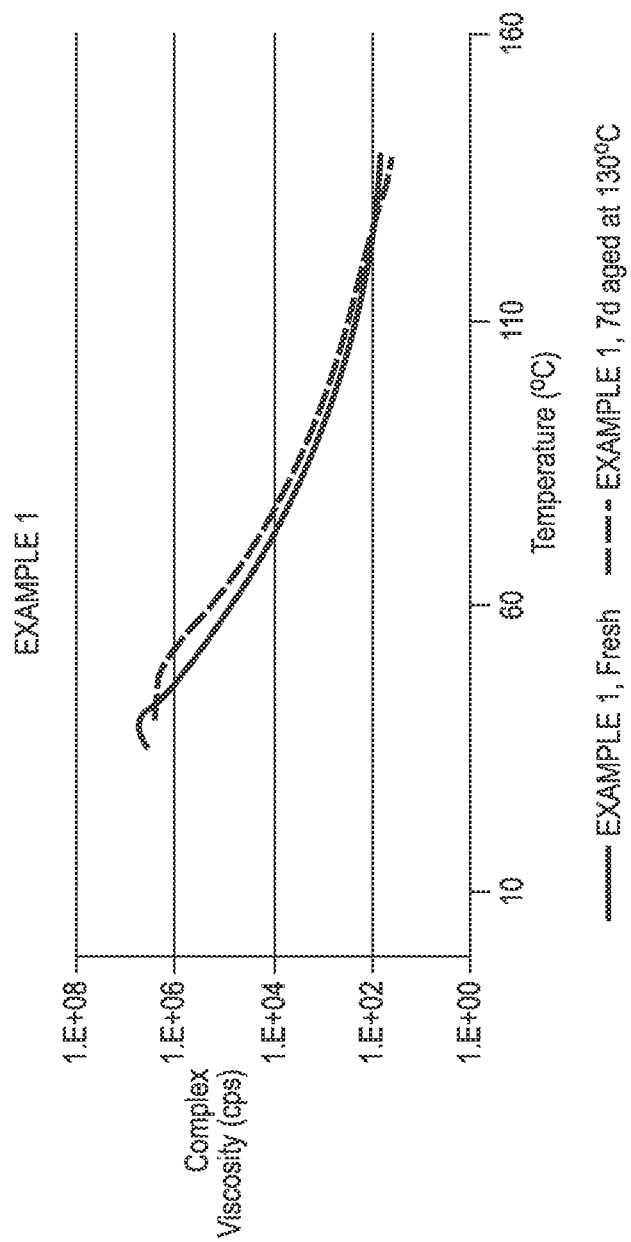
FIG. 1 shows the complex viscosity (y-axis, centipoise) versus temperature (x-axis, ° C.) for an amorphous amine D monoamide compound prepared in accordance with the present disclosure both fresh and aged for seven days at 130° C.

Described is a an amorphous amide compound of the formula

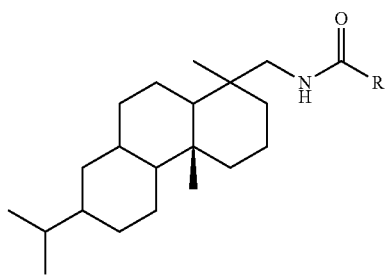

wherein R is an alkyl group having from about 1 to about 22 carbon atoms, and wherein the alkyl group can be selected from linear, branched, saturated, unsaturated, cyclic, substituted, and unsubstituted alkyl groups, and wherein hetero atoms, such as oxygen, nitrogen, sulfur, silicon, boron, phosphorus, and the like may optionally be present in the alkyl group; an aryl group having from about 3 to about 18 carbon atoms including unsubstituted and substituted aryl groups, and wherein hetero atoms, such as oxygen, nitrogen, sulfur, silicon, phosphorus, and the like may optionally be present in the aryl group; an alkylaryl group having from about 4 to about 18 carbon atoms, including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, and the like may optionally be present in either or both of the alkyl portion and the aryl portion of the alkylaryl group; an arylalkyl group having from about 4 to about 18 carbon atoms, including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, and the like may optionally be present in either or both of the alkyl portion and the aryl portion of the arylalkyl group;

and wherein, in embodiments, R is an alkyl group having from about 1 to about 22 carbon atoms, or from about 2 to about 18 carbon atoms, or from about 5 to about 15 carbon atoms, or from about 10 to about 12 carbon atoms.

Also described is an amorphous amide compound of the formula

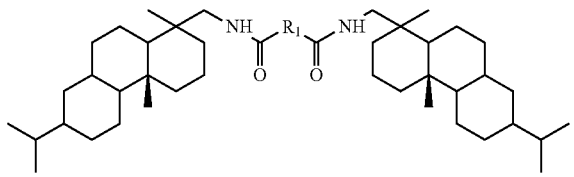

wherein $R_1$ is an alkylene group having from about 1 to about 22 carbon atoms, and wherein the alkylene group can be selected from linear, branched, saturated, unsaturated, cyclic, substituted, and unsubstituted alkyl groups, and wherein hetero atoms, such as oxygen, nitrogen, sulfur, silicon, boron, phosphorus, and the like may optionally be present in the alkylene group; an arylene group having from about 3 to about 18 carbon atoms including unsubstituted and substituted arylene groups, and wherein hetero atoms, such as oxygen, nitrogen, sulfur, silicon, phosphorus, and the like may optionally be present in the arylene group; an alkylarylene group having from about 4 to about 18 carbon atoms, including unsubstituted and substituted alkylarylene groups, wherein the alkyl portion of the alkylarylene group can be linear, branched, saturated, unsaturated, and/or cyclic, and wherein hetero atoms, such as oxygen, nitrogen, sulfur, silicon, phosphorus, and the like may optionally be present in either or both of the alkyl portion and the aryl portion of the alkylarylene group; an arylalkylene group having from about 4 to about 18 carbon atoms, including unsubstituted and substituted arylalkylene groups, wherein the alkyl portion of the arylalkylene group can be linear, branched, saturated, unsaturated, and/or cyclic, and wherein hetero atoms, such as oxygen, nitrogen, sulfur, silicon, phosphorus, and the like may optionally be present in either or both of the alkyl portion and the aryl portion of the arylalkylene group;

and wherein, in embodiments, $R_1$ is an alkylene group having from about 1 to about 22 carbon atoms, or from about 2 to about 18 carbon atoms, or from about 5 to about 15 carbon atoms, or from about 10 to about 12 carbon atoms.

The amorphous amides described herein can be prepared by any suitable or desired method. In embodiments, amine D amorphous amide compounds herein are prepared by reacting amine D with an acid of the formula

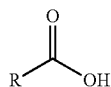

wherein R is an alkyl group having from about 1 to about 22 carbon atoms, and wherein the alkyl group can be selected from linear, branched, saturated, unsaturated, cyclic, substituted, and unsubstituted alkyl groups, and wherein hetero atoms, such as oxygen, nitrogen, sulfur, silicon, boron, phosphorus, and the like may optionally be present in the alkyl group; an aryl group having from about 3 to about 18 carbon atoms including unsubstituted and substituted aryl groups, and wherein hetero atoms, such as oxygen, nitrogen, sulfur, silicon, phosphorus, and the like may optionally be present in the aryl group; an alkylaryl group having from about 4 to about 18 carbon atoms, including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, and the like may optionally be present in either or both of the alkyl portion and the aryl portion of the alkylaryl group; an arylalkyl group having from about 4 to about 18 carbon atoms, including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, and the like may optionally be present in either or both of the alkyl portion and the aryl portion of the arylalkyl group;

and wherein, in embodiments, R is an alkyl group having from about 1 to about 22 carbon atoms, or from about 2 to about 18 carbon atoms, or from about 5 to about 15 carbon atoms, or from about 10 to about 12 carbon atoms;

with mixing, optional heating, such as to a temperature of from about 140° C. to 190° C., or from about 150° C. to 190° C. or from about 160° C. to 180° C., optional catalyst, and under optional vacuum, to produce a monoamide in accordance with the following reaction scheme:

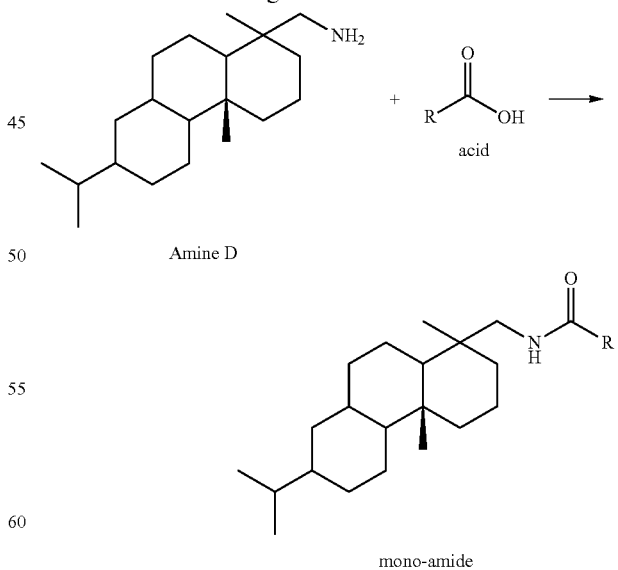

wherein R of the mono-amide product is as described herein for the acid.

The amorphous diamides described herein can be prepared by any suitable or desired method. In embodiments, amine D amorphous diamide compounds herein are prepared by reacting amine D with a diacid of the formula

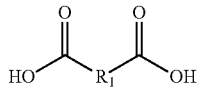

wherein $R_1$ is an alkylene group having from about 1 to about 22 carbon atoms, and wherein the alkylene group can be selected from linear, branched, saturated, unsaturated, cyclic, substituted, and unsubstituted alkyl groups, and wherein hetero atoms, such as oxygen, nitrogen, sulfur, silicon, boron, phosphorus, and the like may optionally be present in the alkylene group; an arylene group having from about 3 to about 18 carbon atoms including unsubstituted and substituted arylene groups, and wherein hetero atoms, such as oxygen, nitrogen, sulfur, silicon, phosphorus, and the like may optionally be present in the arylene group; an alkylarylene group having from about 4 to about 18 carbon atoms, including unsubstituted and substituted alkylarylene groups, wherein the alkyl portion of the alkylarylene group can be linear, branched, saturated, unsaturated, and/or cyclic, and wherein hetero atoms, such as oxygen, nitrogen, sulfur, silicon, phosphorus, and the like may optionally be present in either or both of the alkyl portion and the aryl portion of the alkylarylene group; an arylalkylene group having from about 4 to about 18 carbon atoms, including unsubstituted and substituted arylalkylene groups, wherein the alkyl portion of the arylalkylene group can be linear, branched, saturated, unsaturated, and/or cyclic, and wherein hetero atoms, such as oxygen, nitrogen, sulfur, silicon, phosphorus, and the like may optionally be present in either or both of the alkyl portion and the aryl portion of the arylalkylene group;

and wherein, in embodiments, $R_1$ is an alkylene group having from about 1 to about 22 carbon atoms, or from about 2 to about 18 carbon atoms, or from about 5 to about 15 carbon atoms, or from about 10 to about 12 carbon atoms;

with mixing, optional heating, such as to a temperature of from about 140° C. to 190° C., or from about 150° C. to 190° C. or from about 160° C. to 180° C., optional catalyst, and under optional vacuum, to produce a monoamide in accordance with the following reaction scheme:

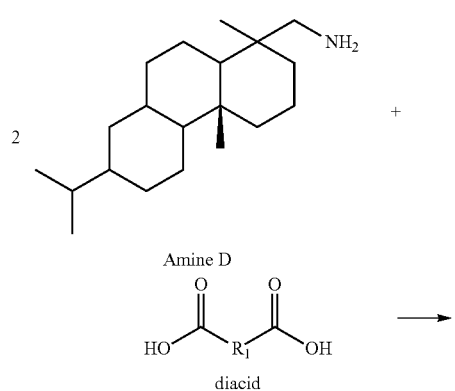

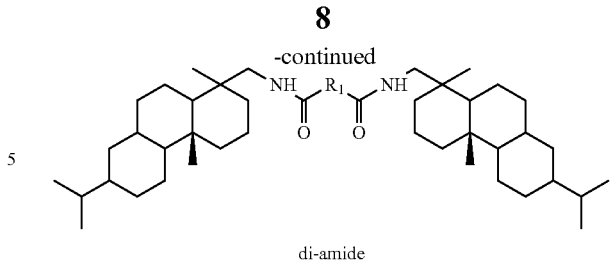

di-amide wherein $R_1$ of the di-amide product is as described herein for the diacid.

In embodiments, phase change ink composition is described comprising an amorphous compound of the formula

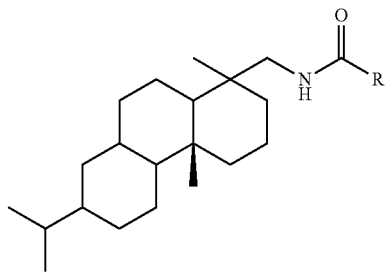

wherein R is selected from the group consisting of an alkyl group, an aryl group, an alkylaryl group, an arylalkyl group, and combinations thereof, as described herein; a crystalline compound; an optional synergist; an optional dispersant; and an optional colorant.

In further embodiments, phase change ink composition is described comprising an amorphous compound of the formula

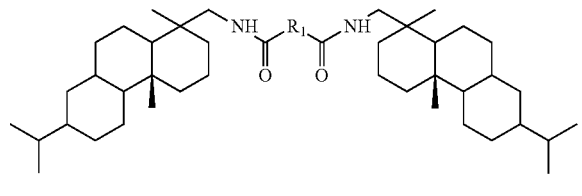

wherein $R_1$ is selected from the group consisting of an alkylene group, an arylene group, an alkylarylene group, an arylalkylene group, and combinations thereof, as described herein; a crystalline compound; an optional synergist; an optional dispersant; and an optional colorant.

The Crystalline Compound.

The crystalline component may comprise amide, aromatic ester, linear diester, urethanes, sulfones, tartaric acid ester derivatives with aromatic groups, or mixtures thereof.

Suitable crystalline components include those disclosed in U.S. patent application Ser. No. 13/457,221 to Morimitsu et al., which is hereby incorporated by reference in its entirety. These crystalline materials comprise the following structure:

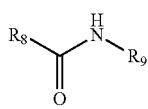

Formula IV wherein $R_8$ and $R_9$ can be the same or different, each $R_8$ and $R_9$ is independently selected from the group consisting of (i) an alkyl group, which can be a linear or branched, cyclic or acyclic, substituted or unsubstituted, saturated or unsaturated, alkyl group, and wherein heteroatoms may optionally be present in the alkyl group, in embodiments, having from about 1 to about 40 carbon atoms, from about 1 to about 20 carbon atoms, or from about 1 to about 10 carbon atoms, (ii) an arylalkyl group, which can be a substituted or unsubstituted arylalkyl group, wherein the alkyl portion of arylalkyl group can be linear or branched, cyclic or acyclic, substituted or unsubstituted, saturated or unsaturated, and wherein heteroatoms may optionally be present in either the aryl portion or the alkyl portion of the arylalkyl group, in embodiments, having from about 4 to about 40 carbon atoms, from about 7 to about 20 carbon atoms, or from about 7 to about 12 carbon atoms; and (iii) an aromatic group, which can be a substituted or unsubstituted aromatic group, wherein the substituent can be a linear, branched, cyclic or acyclic alkyl group and wherein heteroatoms may optionally be present in the aromatic group, having from about 3 to about 40 carbon atoms, from about 6 to about 20 carbon atoms, or from about 6 to about 10 carbon atoms.

Suitable crystalline components include those disclosed in U.S. patent application Ser. No. 13/456,916 to Morimitsu et al., which is hereby incorporated by reference in its entirety. These crystalline materials comprise the following structure:

Formula V wherein $R_{10}$ and $R_{11}$ can be the same or different, and wherein each $R_{10}$ and $R_{11}$ is independently selected from the group consisting of (i) an alkyl group, which can be a linear or branched, cyclic or acyclic, substituted or unsubstituted, saturated or unsaturated, alkyl group, and wherein heteroatoms may optionally be present in the alkyl group, in embodiments, having from about 1 to about 40 carbon atoms, from about 1 to about 20 carbon atoms, or from about 1 to about 10 carbon atoms; (ii) an arylalkyl group, which can be a substituted or unsubstituted arylalkyl group, wherein the alkyl portion of arylalkyl group can be linear or branched, cyclic or acyclic, substituted or unsubstituted, saturated or unsaturated, and wherein heteroatoms may optionally be present in either the aryl portion or the alkyl portion of the arylalkyl group, in embodiments, having from about 4 to about 40 carbon atoms, from about 7 to about 20 carbon atoms, or from about 7 to about 12 carbon atoms; and (iii) an aromatic group, which can be a substituted or unsubstituted aromatic group, wherein the substituent can be a linear, branched, cyclic or acyclic alkyl group and wherein heteroatoms may optionally be present in the aromatic group, having from about 3 to about 40 carbon atoms, or about 6 to about 20 carbon atoms, or from about 6 to about 10 carbon atoms, although the numbers can be outside of these ranges, and mixtures thereof, provided that at least one of $R_{10}$ and $R_{11}$ is an aromatic group; and p is 0 or 1.

Non-limited examples of crystalline aromatic ether include

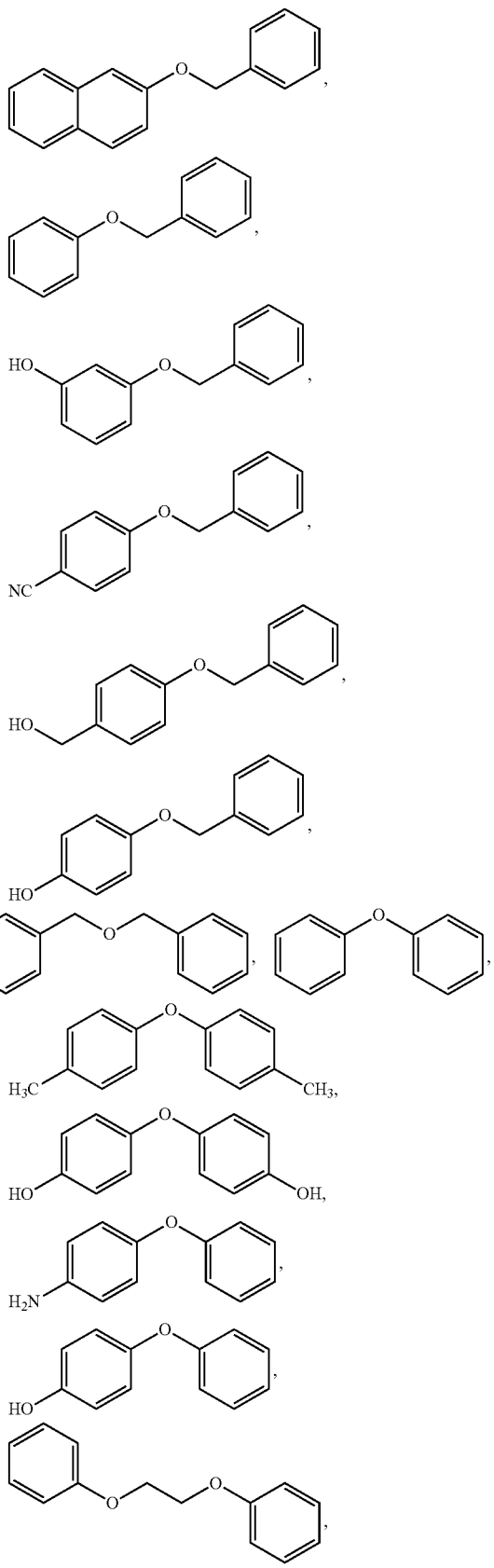

and mixtures thereof.

Suitable crystalline components include those disclosed in U.S. patent application Ser. No. 13/095,555 to Chopra et al., which is hereby incorporated by reference in its entirety. These crystalline materials comprise an ester of an aliphatic linear diacid having the following structure:

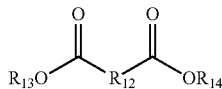

Formula VI wherein $R_{12}$ may be substituted or unsubstituted alkyl chain and is selected from the group consisting of —$(CH_2)_1$— to —$(CH_2)_{12}$—, and wherein $R_{13}$ and $R_{14}$, each independently of the other, is selected from the group consisting of a substituted or unsubstituted aromatic or heteroaromatic group, substituents including alkyl groups, wherein the alkyl portion can be straight, branched or cyclic.

Suitable crystalline components include those disclosed in U.S. patent application Ser. No. 13/456,619 to Chopra et al., which is hereby incorporated by reference in its entirety. These crystalline materials comprise diurethanes having the following structure:

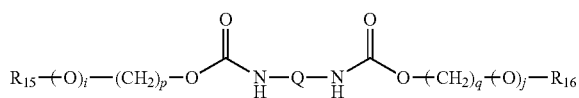

Formula VII wherein Q is alkanediyl; each $R_{15}$ and $R_{16}$ is independently phenyl or cyclohexyl optionally substituted with one or more alkyl; i is 0 or 1; j is 0 or 1; p is 1 to 4; q is 1 to 4. In certain of such embodiments, each $R_{15}$ and $R_{16}$ is independently phenyl or cyclohexyl optionally substituted with one or more methyl or ethyl. In certain of such embodiments, $R_{15}$ and $R_{16}$ is phenyl. In certain embodiments, Q is —$(CH_2)_n$— and n is 4 to 8. In certain of such embodiments, n is 6. In certain embodiments, each $R_{15}$ and $R_{16}$, is independently selected from benzyl, 2-phenylethyl, 2-phenoxyethyl, $C_6H_5(CH_2)_4$—, cyclohexyl, 2-methylcyclohexyl, 3-phenylpropanyl, 3-methylcyclohexyl, 4-methylcyclohexyl, cyclohexylmethyl, 2-methylcyclohexylmethyl, 3-methylcyclohexylmethyl, 4-methylcyclohexylmethyl, and 4-ethylcyclohexanyl.

Suitable crystalline components include those disclosed in U.S. patent application Ser. No. 13/457,323 to Morimitsu et al., which is hereby incorporated by reference in its entirety. These crystalline component being a sulfone compound having the following structure:

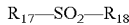

Formula VIII wherein $R_{17}$ and $R_{18}$ can be the same or different, and wherein $R_{17}$ and $R_{18}$ each, independently of the other is selected from the group consisting of (i) an alkyl group, which can be a linear or branched, cyclic or acyclic, substituted or unsubstituted, saturated or unsaturated, alkyl group, and wherein heteroatoms may optionally be present in the alkyl group, in embodiments, having from about 1 to about 40 carbon atoms, from about 1 to about 20 carbon atoms, or from about 1 to about 10 carbon atoms, although the numbers can be outside of these ranges, (ii) an arylalkyl group, which can be a substituted or unsubstituted arylalkyl group, wherein the alkyl portion of arylalkyl group can be linear or branched, cyclic or acyclic, substituted or unsubstituted, saturated or unsaturated, and wherein heteroatoms may optionally be present in either the aryl portion or the alkyl portion of the arylalkyl group, in embodiments, having from about 4 to about 40 carbon atoms, from about 7 to about 20 carbon atoms, or from about 7 to about 12 carbon atoms, although the numbers can be outside of these ranges; and (iii) an aromatic group, which can be a substituted or unsubstituted aromatic group, wherein the substituent can be a linear, branched, cyclic or acyclic alkyl group and wherein heteroatoms may optionally be present in the aromatic group, having from about 3 to from about 40 carbon atoms, from about 6 to about 20 carbon atoms, or about 6 to about 10 carbon atoms, although the numbers can be outside of these ranges, and mixtures thereof.

In certain embodiments, each $R_{17}$ and $R_{18}$ is independently alkyl, or aryl, optionally substituted with one or more halo, amino, hydroxy, or cyano groups and combinations thereof, or $R_{17}$ and $R_{18}$ taken together with the S atom to which they are attached form a heterocyclic ring. In certain of such embodiments, each $R_{17}$ and $R_{18}$ is independently an optionally substituted alkyl, such as, methyl, ethyl, isopropyl, n-butyl, or t-butyl. In certain of such embodiments, each $R_{17}$ and $R_{18}$ is independently an optionally substituted aryl, such as, phenyl, or benzyl. In certain embodiments, each $R_{17}$ and $R_{18}$ is independently substituted with one or more amino, chloro, fluoro, hydroxy, cyano or combinations thereof. Substitution on the aryl groups may be made in the ortho, meta or para position of the phenyl groups and combinations thereof. In certain embodiments, each $R_{17}$ and $R_{18}$ is independently 2-hydroxyethyl, or cyanomethyl.

In certain embodiments, the crystalline component may include diphenyl sulfone, dimethyl sulfone, bis(4-hydroxyphenyl) sulfone, bis(4-aminophenyl) sulfone, bis(3-aminophenyl) sulfone, bis(4-chlorophenyl) sulfone, bis(4-fluorophenyl) sulfone, 2-hycroxyphenyl-4-hydroxyphenyl sulfone, phenyl-4-chlorophenyl sulfone, phenyl-2-aminophenyl sulfone, bis(3-amino-4-hydroxyphenyl) sulfone, dibenzyl sulfone, methylethyl sulfone, diethyl sulfone, methylisopropyl sulfone, ethylisopropyl sulfone, di-n-butyl sulfone, divinyl sulfone, methyl-2-hydroxymethyl sulfone, methylchloromethyl sulfone, sulfolane, 3-sulfolene, and mixtures thereof.

The crystalline compound may comprise an ester of tartaric acid of the following formula:

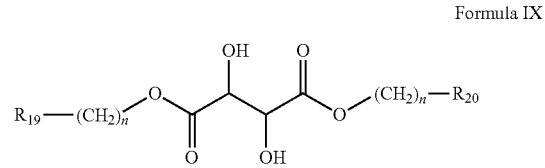

Formula IX wherein each $R_{19}$ and $R_{20}$ is independently an aryl or a heteroaryl optionally substituted with an alkyl group, an alkoxyl group, or a combination thereof, or a lower alkyl and alkoxy, each n is independently 0 to 3. In certain embodiments, each $R_{19}$ and $R_{20}$ is independently an optionally substituted aryl, such as a phenyl. In certain embodiments, each $R_{19}$ and $R_{20}$ is independently not substituted, or substituted with methyl, ethyl, isopropyl, methoxy or ethoxy. In certain embodiments, each $R_{19}$ and $R_{20}$ is independently a phenyl optionally substituted with methyl or methoxy.

In certain embodiments, each $R_{19}$ and $R_{20}$, independently is selected from the group consisting of

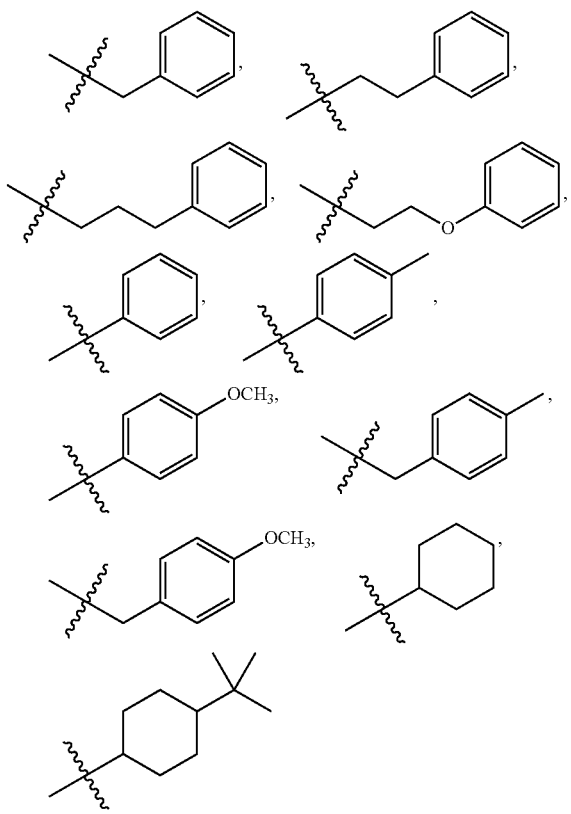

and mixtures thereof.

In certain embodiments, the tartaric acid backbone is selected from L-(+)-tartaric acid, D-(-)-tartaric acid, DL-tartaric acid, or mesotartaric acid, and mixtures thereof.

In certain embodiments, the crystalline compound is selected from the group consisting of dibenzyl L-tartrate, diphenethyl L-tartrate, bis(3-phenyl-1-propyl) L-tartrate, bis(2-phenoxyethyl) L-tartrate, diphenyl L-tartrate, bis(4-methylphenyl) L-tartrate, bis(4-methoxyphenyl) L-tartrate, bis(4-methylbenzyl) L-tartrate, bis(4-methoxybenzyl) L-tartrate, and mixtures thereof.

To synthesize the crystalline materials, a variety of aromatic alcohols may be used in the esterification. Non-limiting exemplary aromatic alcohols include the following

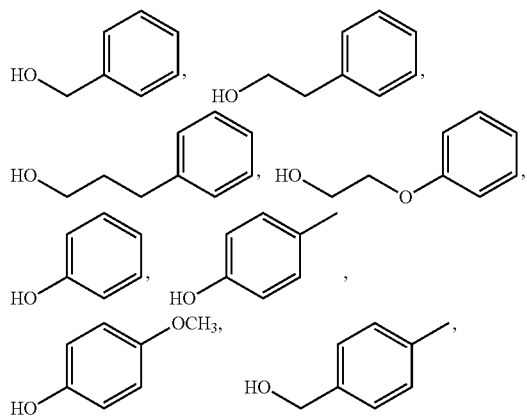
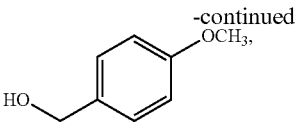

and any stereoisomers and mixtures thereof.

In embodiments, two or more molar equivalents of alcohol may be used in the reaction to produce the di-esters of tartaric acid. If one molar equivalent of alcohol is used, the result is mostly mono-esters.

Colorant.

The phase change ink compositions can include any suitable or desired colorant such as colorants selected from the group consisting of traditional dyes, pigments, and mixtures and combinations thereof present in any suitable or desired amount. If more than one colorant is included, the total amount of colorant present in the phase change ink composition can be any desired or effective amount to obtain the desired color or hue, in embodiments from about 0.1 to about 50 percent, or from about 0.1 percent to about 20 percent total colorant by weight based on the total weight of the phase change ink composition.

Any desired or effective colorant can be employed in the inks, including dyes, pigments, mixtures thereof, and the like, provided that the colorant can be dissolved or dispersed in the ink vehicle. The compositions can be used in combination with conventional ink colorant materials, such as Color Index (C.I.) Solvent Dyes, Disperse Dyes, modified Acid and Direct Dyes, Basic Dyes, Sulphur Dyes, Vat Dyes, and the like.

Examples of suitable dyes include Neozapon® Red 492 (BASF); Orasol® Red G (Pylam Products); Direct Brilliant Pink B (Oriental Giant Dyes); Direct Red 3BL (Classic Dyestuffs); Supranol® Brilliant Red 3BW (Bayer AG); Lemon Yellow 6G (United Chemie); Light Fast Yellow 3G (Shaanxi); Aizen Spilon Yellow C-GNH (Hodogaya Chemical); Bemachrome Yellow GD Sub (Classic Dyestuffs); Cartasol® Brilliant Yellow 4GF (Clariant); Cibanone Yellow 2G (Classic Dyestuffs); Orasol® Black RLI (BASF); Orasol® Black CN (Pylam Products); Savinyl Black RLSN (Clariant); Pyrazol Black BG (Clariant); Morfast® Black 101 (Rohm & Haas); Diaazol Black RN (ICI); Thermoplast® Blue 670 (BASF); Orasol® Blue GN (Pylam Products); Savinyl Blue GLS (Clariant); Luxol Fast Blue MBSN (Pylam Products); Sevron Blue 5GMF (Classic Dyestuffs); Basacid® Blue 750 (BASF); Keyplast Blue (Keystone Aniline Corporation); Neozapon® Black X51 (BASF); Classic Solvent Black 7 (Classic Dyestuffs); Sudan Blue 670 (C.I. 61554) (BASF); Sudan Yellow 146 (C.I. 12700) (BASF); Sudan Red 462 (C.I. 26050) (BASF); C.I. Disperse Yellow 238; Neptune Red Base NB543 (BASF, C.I. Solvent Red 49); Neopen® Blue FF-4012 (BASF); Fastol® Black BR (C.I. Solvent Black 35) (Chemische Fabriek Triade BV); Morton Morplas Magenta 36 (C.I. Solvent Red 172); metal phthalocyanine colorants, such as those disclosed in U.S. Pat. No. 6,221,137, the disclosure of which is totally incorporated herein by reference, and the like. Polymeric dyes can also be used, such as those disclosed in, for example, U.S. Pat. No. 5,621,022 and U.S. Pat. No. 5,231,135, the disclosures of each of which are hereby incorporated by reference herein in their entireties, and commercially available from, for example, Milliken & Company as Milliken Ink Yellow 869, Milliken Ink Blue 92, Milliken Ink Red 357, Milliken Ink Yellow 1800, Milliken Ink Black 8915-67, uncut Reactint® Orange X-38, uncut Reactint® Blue X-17, Solvent Yellow 162, Acid Red 52, Solvent Blue 44, and uncut Reactint® Violet X-80.

In specific embodiments, the phase change ink compositions herein are pigmented phase change ink compositions. In embodiments, the pigment is selected from the group consisting of metal phthalocyanine, metal-free phthalocyanine, and mixtures and combinations thereof. In certain embodiments, the phase change ink composition includes a pigment selected from the group consisting of cyan, green, blue, black, carbon black, Pigment Blue, copper phthalocyanine, and mixtures and combinations thereof. In a specific embodiment, the pigment is a cyan pigment.

Suitable pigments that can be used in embodiments herein include, for example, PALIOGEN® Violet 5100 (commercially available from BASF); PALIOGEN® Violet 5890 (commercially available from BASF); HELIOGEN® Green L8730 (commercially available from BASF); LITHOL® Scarlet D3700 (commercially available from BASF); SUNFAST® Blue 15:4 (commercially available from Sun Chemical); HOSTAPERM® Blue B2G-D (commercially available from Clariant); HOSTAPERM® Blue B4G (commercially available from Clariant); Permanent Red P-F7RK; HOSTAPERM® Violet BL (commercially available from Clariant); LITHOL® Scarlet 4440 (commercially available from BASF); Bon Red® C (commercially available from Dominion Color Company); ORACET® Pink RF (commercially available from Ciba); PALIOGEN® Red 3871 K (commercially available from BASF); SUNFAST® Blue 15:3 (commercially available from Sun Chemical); PALIOGEN® Red 3340 (commercially available from BASF); SUNFAST® Carbazole Violet 23 (commercially available from Sun Chemical); LITHOL® Fast Scarlet L4300 (commercially available from BASF); SUNBRITE® Yellow 17 (commercially available from Sun Chemical); HELIOGEN® Blue L6900, L7020 (commercially available from BASF); SUNBRITE® Yellow 74 (commercially available from Sun Chemical); SPECTRA® PAC C Orange 16 (commercially available from Sun Chemical); HELIOGEN® Blue K6902, K6910 (commercially available from BASF); SUNFAST® Magenta 122 (commercially available from Sun Chemical); HELIOGEN® Blue D6840, D7080 (commercially available from BASF); Sudan Blue OS (commercially available from BASF); NEOPEN® Blue FF4012 (commercially available from BASF); PV Fast Blue B2GO1 (commercially available from Clariant); IRGALITE® Blue BCA (commercially available from Ciba); PALIOGEN® Blue 6470 (commercially available from BASF); Sudan Orange G (commercially available from Aldrich), Sudan Orange 220 (commercially available from BASF); PALIOGEN® Orange 3040 (BASF); PALIOGEN® Yellow 152, 1560 (commercially available from BASF); LITHOL® Fast Yellow 0991 K (commercially available from BASF); PALIOTOL® Yellow 1840 (commercially available from BASF); NOVOPERM® Yellow FGL (commercially available from Clariant); Ink Jet Yellow 4G VP2532 (commercially available from Clariant); Toner Yellow HG (commercially available from Clariant); Lumogen® Yellow D0790 (commercially available from BASF); Suco-Yellow L1250 (commercially available from BASF); Suco-Yellow D1355 (commercially available from BASF); Suco Fast Yellow D1 355, D1 351 (commercially available from BASF); HOSTAPERM® Pink E 02 (commercially available from Clariant); Hansa Brilliant Yellow 5GX03 (commercially available from Clariant); Permanent Yellow GRL 02 (commercially available from Clariant); Permanent Rubine L6B 05 (commercially available from Clariant); FANAL® Pink D4830 (commercially available from BASF); CINQUASIA® Magenta (commercially available from DU PONT); PALIOGEN® Black L0084 (commercially available from BASF); Pigment Black K801 (commercially available from BASF); and carbon blacks such as REGAL® 330 (commercially available from Cabot), Nipex® 150 (commercially available from Degussa) Carbon Black 5250 and Carbon Black 5750 (commercially available from Columbia Chemical), and the like, as well as mixtures thereof.

The pigment can be provided in the phase change ink composition in any suitable or desired amount. In embodiments, the pigment can be present in an amount of from about 0.1 to about 20 percent, or from about 0.5 percent to about 5 percent, or about 0.75 to about 3 percent total pigment, based on the total weight of the phase change ink composition.

Synergist.

The phase change ink compositions here in optionally further comprise a synergist. Any suitable or desired synergist can be employed. In embodiments, a copper phthalocyanine derivative is employed as a synergist for improving dispersion stability of pigmented phase change inks, in embodiments cyan phase change inks.

Dispersant.

The phase change ink compositions herein can contain a dispersant. Any suitable or desired dispersant can be employed. In embodiments, the dispersant can be a dispersant described in U.S. Pat. No. 7,973,186 of Adela Goredema, et al., which is hereby incorporated by reference herein in its entirety. In specific embodiments, the dispersant is a compound of the formula

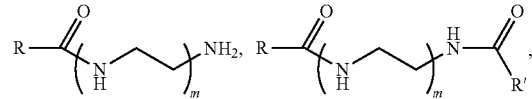

or a mixture thereof; wherein R and R' are the same or different, and wherein R and R' are independently selected from a linear alkyl group having about 37 carbon atoms and a linear alkyl group having about 47 carbon atoms; and wherein m is an integer of from about 1 to about 30.

The dispersant can optionally be a polymeric dispersant such as those sold under the name Solsperse®, in embodiments, Solsperse® 1700, Solsperse® 32000, Solsperse® 13240, available from The Lubrizol Corporation.

The dispersant can be provided in the phase change ink composition in any suitable or desired amount. In embodiments, the dispersant can be present in an amount of from about 1 to about 500 percent, or from about 10 to about 300 percent, or from about 30 to about 200 percent total dispersant, based on the total weight of the pigment in the phase change ink composition.

Other Additives.

The ink may further include conventional additives to take advantage of the known functionality associated with such conventional additives. Such additives may include, for example, at least one antioxidant, defoamer, slip and leveling agents, clarifier, viscosity modifier, adhesive, plasticizer and the like.

The ink may optionally contain antioxidants to protect the images from oxidation and also may protect the ink components from oxidation while existing as a heated melt in the ink reservoir. Examples of suitable antioxidants include N,N'-hexamethylene bis(3,5-di-tert-butyl-4-hydroxy hydrocinnamamide) (IRGANOX® 1098, available from BASF); 2,2-bis(4-(2-(3,5-di-tert-butyl-4-hydroxyhydrocinnamoyloxy)) ethoxyphenyl)propane (TOPANOL-205, available from Vertellus); tris(4-tert-butyl-3-hydroxy-2,6-dimethyl benzyl)isocyanurate (Aldrich); 2,2'-ethylidene bis(4,6-di-tert-butylphenyl)fluoro phosphonite (ETHANOX® 398, available from Albermarle Corporation); tetrakis(2,4-di-tert-butylphenyl)-4,4'-biphenyl diphosphonite (Aldrich); pentaerythritol tetrastearate (TCI America); tributylammonium hypophosphite (Aldrich); 2,6-di-tert-butyl-4-methoxyphenol (Aldrich); 2,4-di-tert-butyl-6-(4-methoxybenzyl)phenol (Aldrich); 4-bromo-2,6-dimethylphenol (Aldrich); 4-bromo-3,5-didimethylphenol (Aldrich); 4-bromo-2-nitrophenol (Aldrich); 4-(diethyl aminomethyl)-2,5-dimethylphenol (Aldrich); 3-dimethylaminophenol (Aldrich); 2-amino-4-tert-amylphenol (Aldrich); 2,6-bis(hydroxymethyl)-p-cresol (Aldrich); 2,2'-methylenediphenol (Aldrich); 5-(diethylamino)-2-nitrosophenol (Aldrich); 2,6-dichloro-4-fluorophenol (Aldrich); 2,6-dibromo fluoro phenol (Aldrich); α-trifluoro-o-cresol (Aldrich); 2-bromo-4-fluorophenol (Aldrich); 4-fluorophenol (Aldrich); 4-chlorophenyl-2-chloro-1,1,2-trifluoroethyl sulfone (Aldrich); 3,4-difluoro phenylacetic acid (Adrich); 3-fluorophenylacetic acid (Aldrich); 3,5-difluoro phenylacetic acid (Aldrich); 2-fluorophenylacetic acid (Aldrich); 2,5-bis(trifluoromethyl) benzoic acid (Aldrich); ethyl-2-(4-(4-(trifluoromethyl)phenoxy)phenoxy)propionate (Aldrich); tetrakis(2,4-di-tert-butyl phenyl)-4,4'-biphenyl diphosphonite (Aldrich); 4-tert-amyl phenol (Aldrich); 3-(2H-benzotriazol-2-yl)-4-hydroxy phenethylalcohol (Aldrich); NAUGARD® 76, NAUGARD® 445, NAUGARD® 512, and NAUGARD® 524 (manufactured by Chemtura Corporation); and the like, as well as mixtures thereof. The antioxidant, when present, may be present in the ink in any desired or effective amount, such as from about 0.25 percent to about 10 percent by weight of the ink or from about 1 percent to about 5 percent by weight of the ink.

The phase ink compositions of the present disclosure can be prepared by any desired or suitable method. In embodiments, a method for preparing a phase change ink composition herein comprises combining an amorphous compound as described herein; a crystalline compound; an optional colorant; an optional synergist; an optional dispersant; to produce a phase change ink composition.

For example, the ink ingredients can be mixed together, followed by heating, to a temperature of at least about 100° C. to no more than about 140° C., although the temperature can be outside of this range, and stirring until a homogeneous ink composition is obtained, followed by cooling the ink to ambient temperature (typically from about 20 to about 25° C.). The inks of the present disclosure are solid at ambient temperature. In a specific embodiment, during the formation process, the inks in their molten state are poured into molds and then allowed to cool and solidify to form ink sticks.

In embodiments, an ink jet printer stick or pellet herein contains a phase change ink composition comprising an amorphous compound as described herein; a crystalline compound; an optional synergist; an optional dispersant; and an optional colorant.

The inks disclosed herein can be employed in apparatus for direct printing ink jet processes and in indirect (offset) printing ink jet applications. Another embodiment is directed to a process which comprises incorporating an ink as disclosed herein into an ink jet printing apparatus, melting the ink, and causing droplets of the melted ink to be ejected in an imagewise pattern onto a recording substrate. A direct printing process is also disclosed in, for example, U.S. Pat. No. 5,195,430, the disclosure of which is totally incorporated herein by reference. The inks prepared as disclosed herein can be employed in apparatus for indirect (offset) printing ink jet applications. Another embodiment is directed to a process which comprises incorporating an ink prepared as disclosed herein into an ink jet printing apparatus, melting the ink, causing droplets of the melted ink to be ejected in an imagewise pattern onto an intermediate transfer member, and transferring the ink in the imagewise pattern from the intermediate transfer member to a final recording substrate. In a specific embodiment, the intermediate transfer member is heated to a temperature above that of the final recording sheet and below that of the melted ink in the printing apparatus. An offset or indirect printing process is also disclosed in, for example, U.S. Pat. No. 5,389,958, the disclosure of which is totally incorporated herein by reference. In one specific embodiment, the printing apparatus employs a piezoelectric printing process wherein droplets of the ink are caused to be ejected in imagewise pattern by oscillations of piezoelectric vibrating elements.

In embodiments, a method herein comprises incorporating into an ink jet printing apparatus a phase change ink composition as described herein; melting the ink composition; and causing droplets of the melted ink to be ejected in an imagewise pattern onto a substrate.

The ink compositions generally have melt viscosities at the jetting temperature (in one embodiment no lower than about 50° C., in another embodiment no lower than about 60° C., and in yet another embodiment no lower than about 70° C., and in one embodiment no higher than about 140° C., and in another embodiment no higher than about 110° C., although the jetting temperature can be outside of these ranges) in one embodiment of no more than about 30 centipoise, in another embodiment of no more than about 20 centipoise, and in yet another embodiment of no more than about 15 centipoise, and in one embodiment of no less than about 2 centipoise, in another embodiment of no less than about 5 centipoise, and in yet another embodiment of no less than about 7 centipoise, in another embodiment, of greater than about $10^7$ centipoise at a temperature of less than about 40° C., in another embodiment, of less than about 15 centipoise at a temperature of no less than about 70° C., although the melt viscosity can be outside of these ranges.

In one specific embodiment, the inks are jetted at low temperatures, in particular at temperatures below about 130° C., in one embodiment from about 40° C. to about 130° C., in another embodiment from about 50° C. to about 130° C., and in yet another embodiment from about 60° C. to about 120° C., although the jetting temperature can be outside of these ranges.

Any suitable substrate or recording sheet can be employed, including plain papers such as XEROX® 4024 papers, XEROX® Image Series papers, Courtland 4024 DP paper, ruled notebook paper, bond paper, silica coated papers such as Sharp Company silica coated paper, JuJo paper, HAMMERMILL LASERPRINT® paper, and the like, transparency materials, fabrics, textile products, plastics, polymeric films, inorganic substrates such as metals and wood, and the like.

EXAMPLES

The following Examples are being submitted to further define various species of the present disclosure. These Examples are intended to be illustrative only and are not intended to limit the scope of the present disclosure. Also, parts and percentages are by weight unless otherwise indicated.

Amine D, a terpenoid compound available from Eastman Chemical Company, is derived from dehydroabeitic acid as the backbone material. These materials are well-suited for amorphous materials owing to their polycyclic nature, and are more sustainable since they are derived from pine which is a renewable resource. Amine D was reacted with 2 mono- and diacids to make the mono- and diamides described below.

Example 1

Synthesis of Amorphous Amine D Monoamide. An amorphous amine D monoamide was prepared according to the following reaction scheme wherein the acid was hexanoic acid wherein R=$C_5H_{10}$ and wherein the hexanoic acid had an acid value of 4.1.

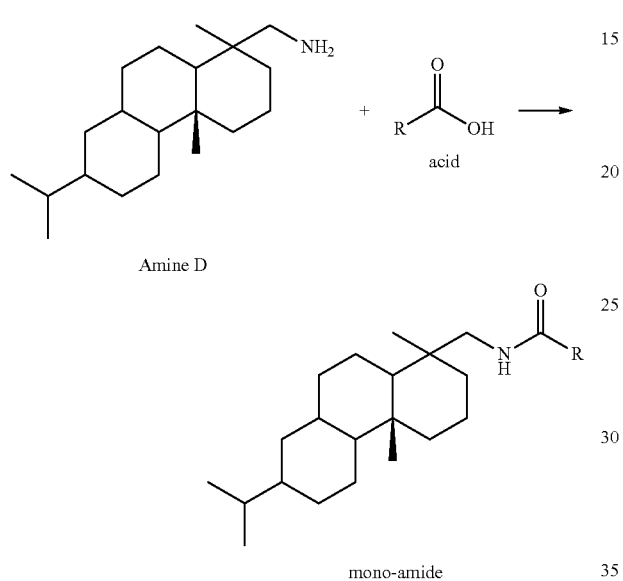

To a 3 neck 250 milliliter round bottomed flask equipped with a dean stark trap and condenser, thermocouple and argon inlet was added Amine D (42.27 grams, 145 mmoles, available from Eastman Chemical Company) and hexanoic acid (16.84 grams, 145 mmoles, available from Sigma-Aldrich®). The mixture was slowly heated under argon to 160° C. during which reagents melted/dissolved. The temperature was raised to 180° C. The reaction mixture was stirred at 180° C. overnight (~20 hours) during which time 2.6 milliliters was collected in dean stark trap. Vacuum was applied (1-2 mm-Hg) for about 10 minutes. The mixture was then cooled under argon to about 140° C. and discharged in an aluminum tray, cooled to room temperature to give 53.8 grams (95% yield) product as tacky light brown solid. $^1$H NMR indicated that the desired product of the formula

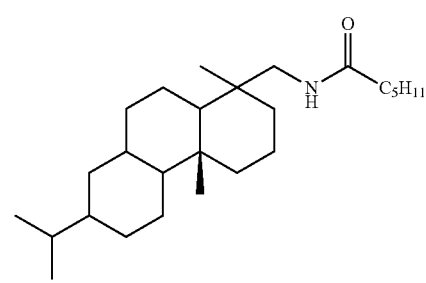

was formed.

Example 2

Synthesis of Amorphous Amine D Monoamide. The preparation of amorphous amine D monoamide according to Example 1 was repeated a second time to establish reproducibility. $^1$H NMR indicated that the desired product of the formula

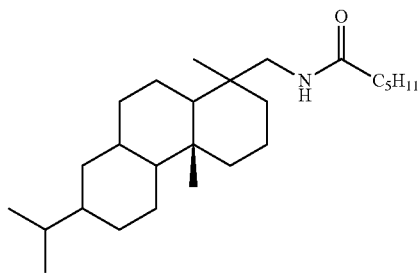

was formed.

Example 3

Synthesis of Amorphous Amine D Monoamide. An amorphous amine D monoamide was prepared according to Example 1 except wherein the acid was 2-ethylhexanoic acid wherein R=$C_8H_{15}$. $^1$H NMR indicated that the desired product of the formula

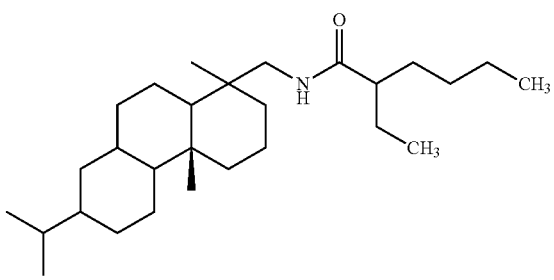 [SMILES: CCCCC(CC)C(=O)NCC1(C)CCC[C@]2(C)C3CCC(C(C)C)CC3CCC12]

was formed.

Example 4

Synthesis of Amorphous Amine D Monoamide. An amorphous amine D monoamide was prepared according to Example 1 except wherein the acid was stearic acid wherein R=$C_{17}H_{36}$. $^1$H NMR indicated that the desired product of the formula

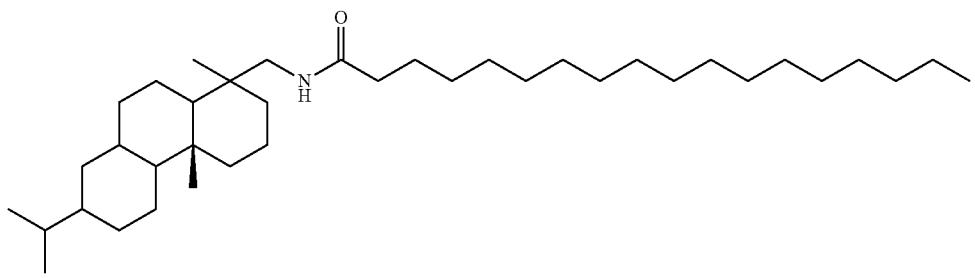 [SMILES: CCCCCCCCCCCCCCCCCC(=O)NCC1(C)CCC[C@]2(C)C3CCC(C(C)C)CC3CCC12]

was formed.

Table 1 provides a summary of the properties of the materials of Examples 1-4. For Examples 1 and 2 (duplicate preparations of the same material), the only difference was the acid number of the product, which is a measure of residual acid starting material in the product. The glass transition temperature (Tg) and viscosity of the amorphous monoamide are unaffected by the acid number.

TABLE 1

| Example | R | Acid Value | Tg (° C.) | Viscosity @ 140° C. (cps) |
|---|---|---|---|---|
| 1 | Hexanoic Acid | 4.1 | 10 | 41.8 |
| 2 | Hexanoic Acid | 22.9 | 9.5 | 30 |
| 3 | 2-ethylhexanoic acid | 25.3 | ND | |
| 4 | Stearic Acid | 14 | Semicrystalline (Tmelt 28 & 41; Tcry 6.7) | ND |

It is desirable for robust phase change ink to have ink components that are stable at the high ink jetting temperatures for a prolonged period of time. The compound of Example 1 was aged in an oven at 130° C. in the presence of an antioxidant (0.03 weight % NAUGARD® 524 (antioxidant available from Chemtura Corporation) for seven days to test its stability. FIG. 1 shows the rheology of the aged and fresh samples which do not show a significant increase in viscosity on aging indicating that this material is stable at high jetting temperatures.

Example 5

Synthesis of Amorphous Amine D Diamide. An amorphous amine D diamide was prepared according to the following reaction scheme wherein the acid was succinic acid wherein $R_1=C_2H_4$.

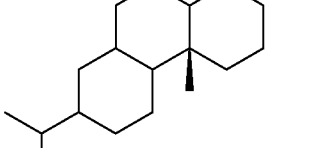

Amine D

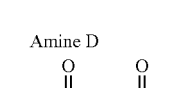

diacid

di-amide

To a 3 neck 10 milliliter round bottomed flask equipped with a dean stark trap and condenser, thermocouple and argon inlet was added Amine D (10 grams, 34.3 mmoles, available from Eastman Chemical Company) and succinic acid (2.03 grams, 17.15 mmoles, available from Sigma-Aldrich®). The mixture was slowly heated under argon to 160° C. during which reagents melted/dissolved. The temperature was raised to 180° C. and the reaction mixture was stirred at 180° C. overnight (about 20 hours) during which a few droplets of water were collected in a dean stark trap. Vacuum (1-2 mm-Hg) was applied for about 10 minutes. The mixture was cooled under argon to about 140° C., discharged into an aluminum tray, cooled to room temperature to give 10.5 grams (92% yield) product as a light brown solid glassy material. $^1$H NMR indicated that the desired product of the formula

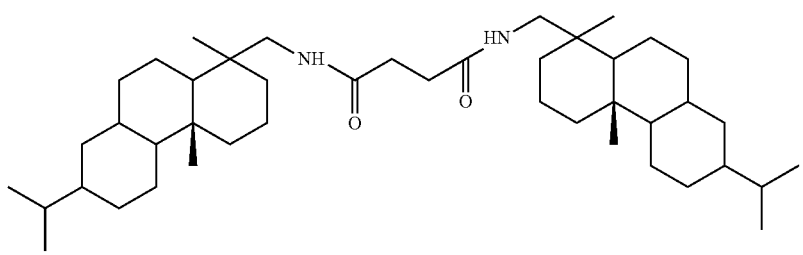 [SMILES: CC(C)C1CCC2C(CCC3C(C)(CNC(=O)CCC(=O)NCC4(C)CCC[C@]5(C)C6CCC(C(C)C)CC6CCC45)CCC[C@@]23C)C1]

was formed.

Example 6

Synthesis of Amorphous Amine D Diamide. An amorphous amine D diamide was prepared according to Example 5 except wherein the diacid was azelaic acid wherein R=$C_7H_{14}$. $^1$H NMR indicated that the desired product of the formula

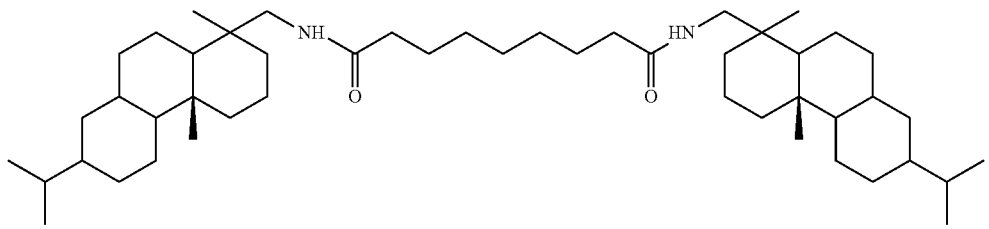 [SMILES: CC(C)C1CCC2C(CCC3C(C)(CNC(=O)CCCCCCCC(=O)NCC4(C)CCC[C@]5(C)C6CCC(C(C)C)CC6CCC45)CCC[C@@]23C)C1]

was formed.

Figure 2:
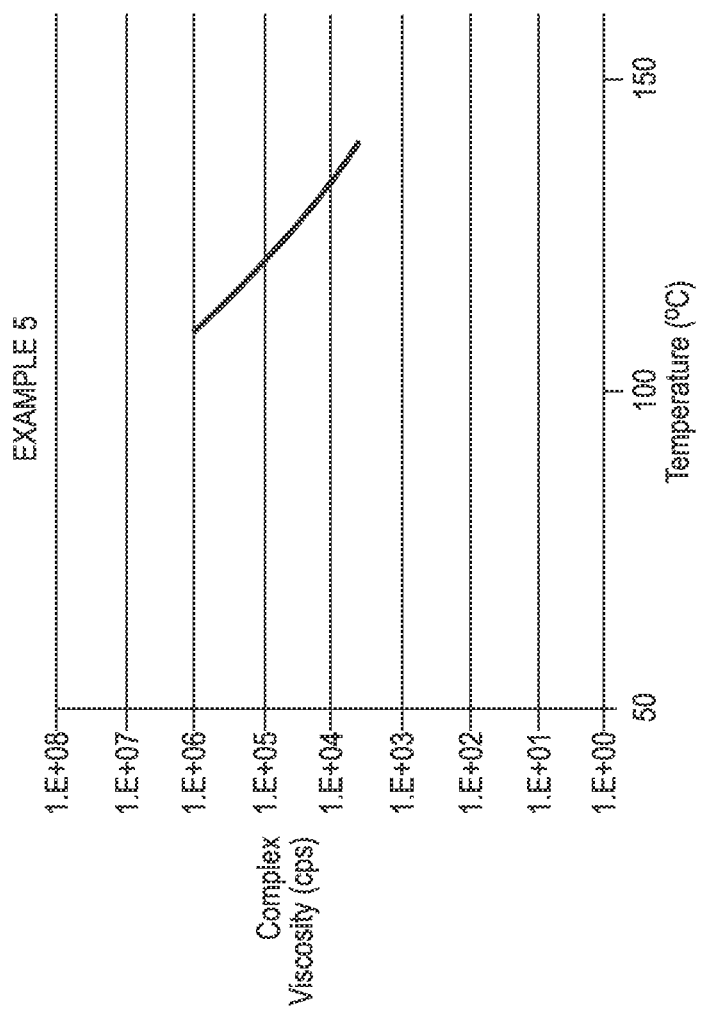
FIG. 2 shows the complex viscosity (y-axis, centipoise) versus temperature (x-axis, ° C.) for an amorphous amine D diamide compound prepared in accordance with the present.
Figure 3:
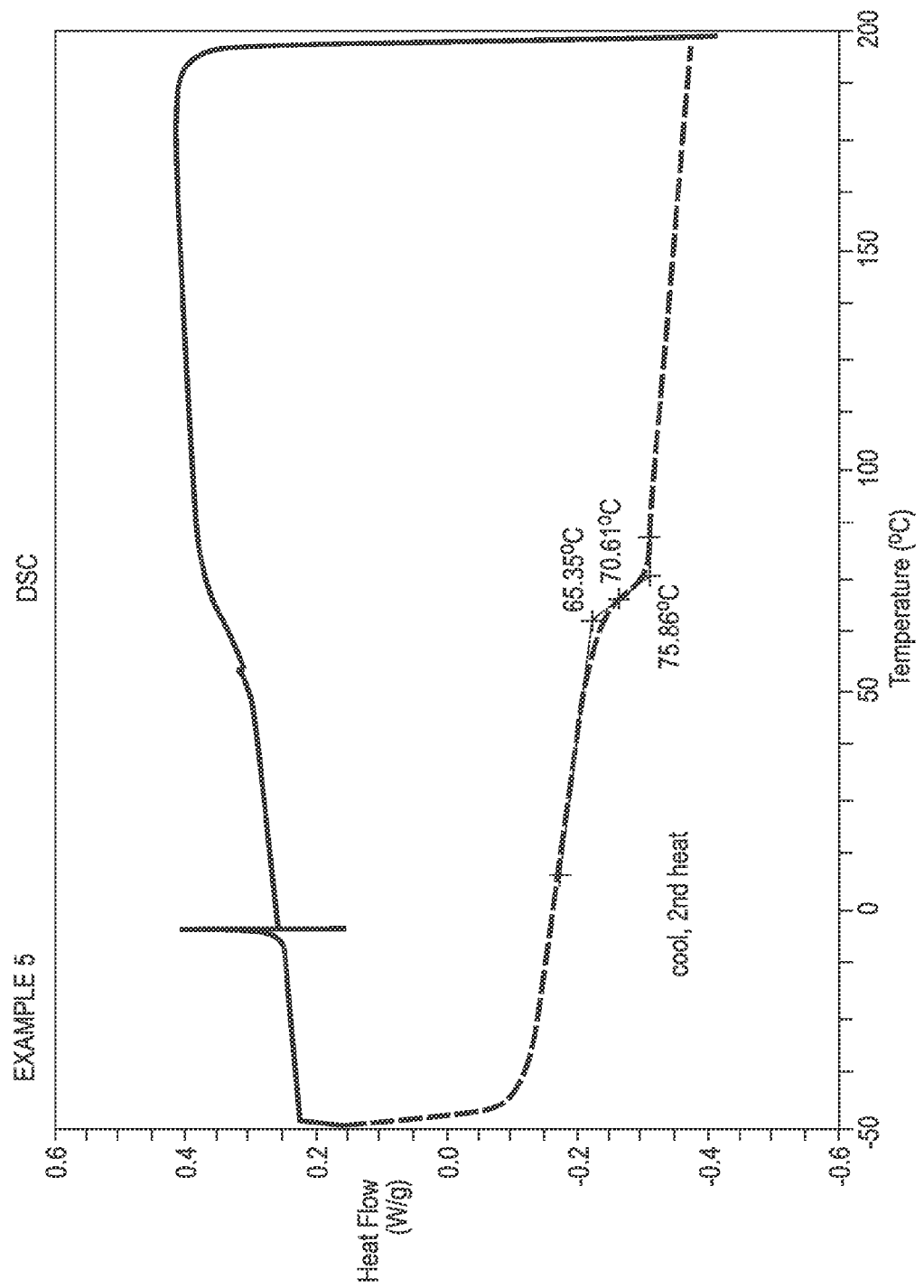
FIG. 3 shows heat flow (y-axis, W/g) versus temperature (x-axis, ° C.) for an amorphous diamide prepared in accordance with the present disclosure.

The viscosity and thermal analysis of the amorphous diamide of Example 5 was measured. FIG. 2 shows the complex viscosity (y-axis, centipoise) versus temperature (x-axis, ° C.) for the amorphous diamide of Example 5. FIG. 3 shows heat flow (y-axis, W/g) versus temperature (x-axis, ° C.) for the amorphous diamide of Example 5. The rheology trace is consistent with an amorphous compound and DSC (Differential Scanning calorimetry) showed a Tg (glass transition temperature) of 70.6° C.

Ink Formulations.

Three inks containing an amorphous monoamide were prepared in combination with the following crystalline materials:

1. Distearyl terephthalate (DST, crystalline);
2. N-phenylethylbenzamide (crystalline); and
3. N-stearybenzamide (crystalline).

Example 7

A pigment concentrate was prepared as follows.

1. Weigh the Solsperse®, synergist, and resin into a beaker.
2. Stir at 140° C. for 30 minutes in heating block.
3. Weigh pigment on analytical balance in a plastic pan. Add to mixture slowly so pigment does not clump.
4. Stir additional 2 hours to ensure the pigment is properly wetted at 140° C. then take out stir bar.
5. Homogenize with homogenizer 20 minutes at 13000 RPM.
6. Attritor: 24 hours at 130° C. bath temp The inks of Examples 8, 9, and 10 were prepared according to the formulations shown in Tables 2, 3, and 4, respectively. For each example, the pigment concentrate of Example 7 was added to the components of Example 8, 9, and 10, with mixing, heating, filtering, discharging as follows. To a 30 milliliter amber glass bottle was added the crystalline and amorphous components, along with a magnetic stir bar. The bottle was transferred to a heating mantle equipped with stiffing capability, and mixed with heating to 130° C. for 1 hour. Once the crystalline and amorphous components had melted to form a homogeneous mixture, pigment dispersion (in either a crystalline or amorphous resin binder) was added and the mixture was stirred for an additional 30 minutes. Finally, the magnet was removed from the bottle and the molten ink mixture was poured into a foil pan to cool and solidify.

TABLE 2

Ink Example 8

| Component | Weight Percent | Mass (Grams) |
|---|---|---|
| Distearyl Terephthalate (DST, crystalline) | 67.55 | 6.75 |
| Amorphous Diamide of Example 2 | 19.12 | 1.91 |
| Pigment concentrate of Example 7 | 13.33 | 1.33 |
| TOTAL | 100.00 | 10 |

TABLE 3

Ink Example 9

| Component | Weight Percent | Mass (Grams) |
|---|---|---|
| N-phenylethylbenzamide (crystalline) | 66.7 | 6.67 |
| Amorphous Diamide of Example 1 | 20.0 | 2.00 |
| Pigment concentrate of Example 7 | 13.3 | 1.33 |
| TOTAL | 100.00 | 10.00 |

TABLE 4

Ink Example 10

| Component | Weight Percent | Mass (Grams) |
|---|---|---|
| N-stearylbenzamide (crystalline) | 66.7 | 6.67 |
| Amorphous Diamide of Example 1 | 20.0 | 2.00 |
| Pigment concentrate of Example 7 | 13.3 | 1.33 |
| TOTAL | 100.00 | 10.00 |

Ink Properties.

Figure 4:
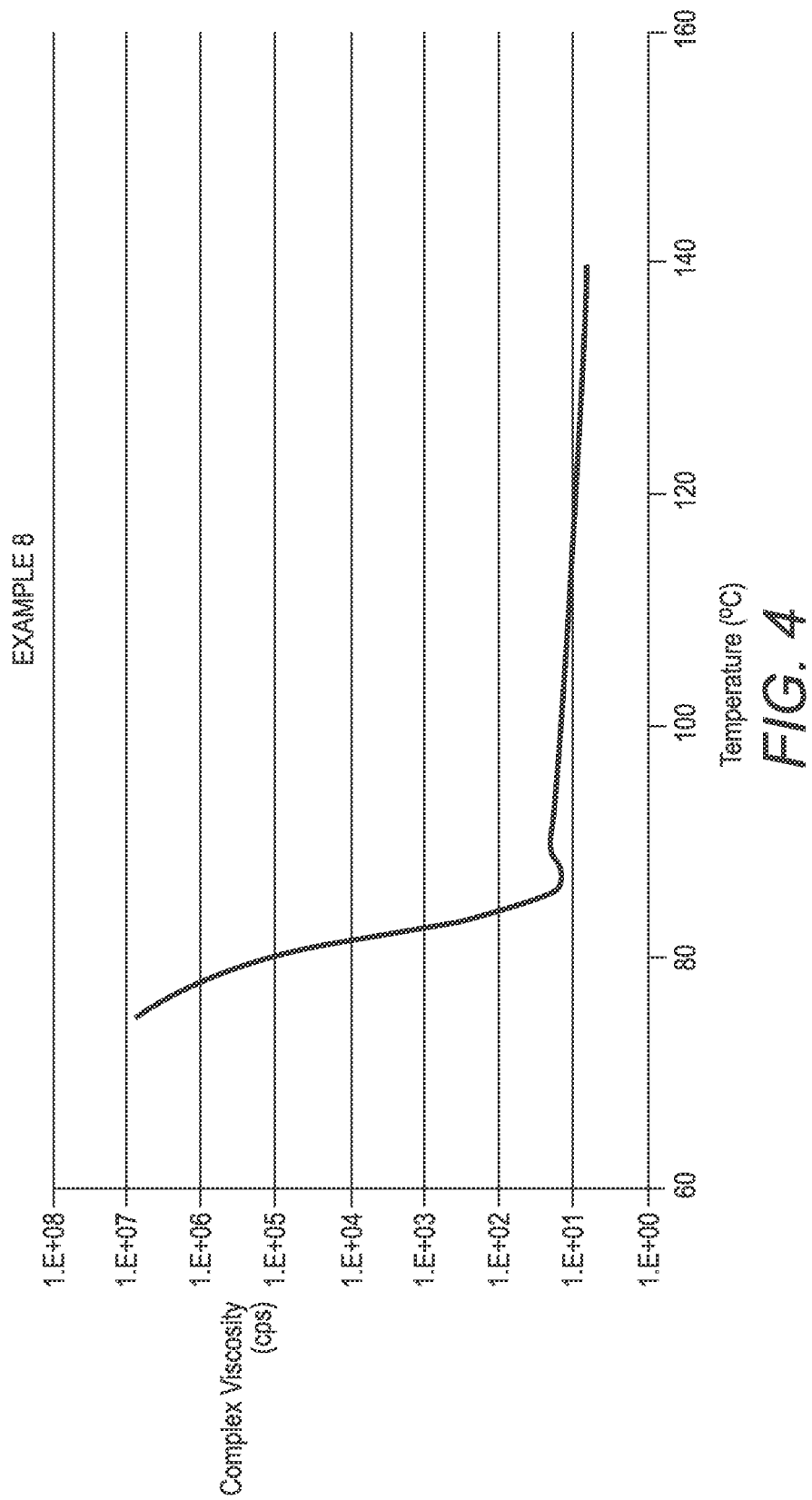
FIG. 4 shows complex viscosity (y-axis, centipoise) versus temperature (x-axis, ° C.) for an ink containing an amorphous amine D monoamide compound prepared in accordance with the present disclosure.

Ink rheology was measured for the inks of Examples 8, 9, and 10. FIG. 4 shows complex viscosity (y-axis, centipoise) versus temperature (x-axis, ° C.) for the ink of Example 8 containing the amorphous monoamide of Example 2. The viscosity measurements shown in Table 5 illustrate that the example ink formulations have the appropriate viscosity at 140° C. for jetting (about 10 centipoise).

TABLE 5

| Ink Example | Viscosity at 140° C. (centipoise) |
|---|---|
| 8 | 7.46 |
| 9 | 11.39 |
| 10 | 6.29 |

Comparative Example 11

A cyan ink was prepared as follows. A cyan ink commercially sold as ColorWave® 300 cyan ink was purchased from Océ.

Comparative Example 12

A Xerox® Phaser® 4200 solid ink cartridge suitable for use in a Xerox® Phaser® 4200 Printer was purchased from Xerox®.

Comparative Example 13

A cyan ink was prepared as follows having the formulation as shown in Table 6.

TABLE 6

| Component | Weight Percent | Mass (Grams) |
|---|---|---|
| Dibenzyl HDI diurethane (crystalline) | 76.48 | 497.1 |
| Amorphous dimenthyl tartrate (DMT) | 3.52 | 22.88 |
| Pigment concentrate | 20 | 130 |
| TOTAL | 100.00 | 650 |

The pigment dispersion was placed in an 80° C. oven for 30 minutes. The pigment dispersion was added to the reactor and allowed to cool. DMT and crystalline compound were added at room temperature. The mixture was then placed in a 140° C. oven for 1 hour, covered tight with aluminum foil. The mixture was then homogenized in a jacketed heater at 140° C. for 30 minutes and then poured into a heated filtration apparatus and filtered.

Dibenzyl HDI Diurethane Preparation.

Into a 16 ounce jar equipped with a magnetic stirrer was charged 120 grams benzyl alcohol (MW=108, 1.11 mmol) and 10 drops of Fascat® 4202 catalyst. The jar was placed in an about 130° C. oil bath. Then 93.3 grams HDI (MW=168, 0.56 mmol) was added. Exothermal was observed. Infrared spectra was determined after 1 hour of reaction and showed no isocyanate peak. The reaction contents were poured into a tin pan to cool and solidify.

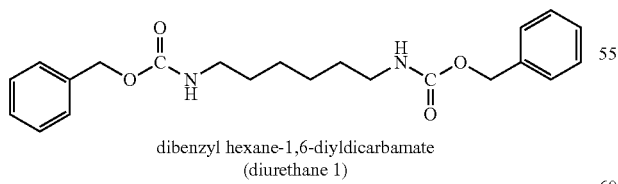

dibenzyl hexane-1,6-diyldicarbamate
(diurethane 1)

DMT (Amorphous) Preparation.

Synthesis of di-DL-menthyl L-tartrate (DMT). L-tartaric acid (18.0 grams, 120 mmol), DL-menthol (37.5 grams, 240 mmol), and xylene (240 milliliters) were added to a 500 milliliter flask, equipped with a Dean-Stark trap, to give a suspension. p-toluenesulfonic acid monohydrate (0.29 grams, 1.5 mmol) was added and the mixture was refluxed for 18 hours with azeotropic removal of water. The reaction mixture was cooled down to room temperature and washed with 10 weight percent KOH aqueous (1×) and brine (2×), then dried over $MgSO_4$. After filtration and removal of the solvent, the residue was dried under vacuum with stirring at 120° C. to obtain 34.9 grams (yield: 68%) of amorphous solid. The sample was characterized by $^1H$ NMR and acid number analysis (1.23 mg KOH/g).

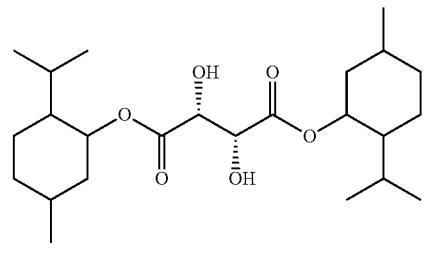

Di-DL-menthyl tartrate (DMT)

Pigment Concentrate Preparation.

A pigment concentrate having the formulation as shown in Table 7 was prepared.

1. The Solsperse®, synergist and DMT were weighed into a beaker.
2. The materials were stirred at 140° C. for 30 minutes in a heating block.
3. The pigment was weighed on an analytical balance in a plastic pan and added to the mixture slowly so that the pigment did not clump.
4. The materials were stirred an additional 2 hours to ensure the pigment was properly wetted at 140° C. and then the stir bar was removed.
5. The materials were homogenized in a Polytron® Homogenizer, available from Metrohm USA, for 20 minutes at 13000 RPM.
6. The materials were then treated in a Szegvari 01 attritor (Union Process) for 24 hours at 110° C.

TABLE 7

| B4G Pigment Concentrate | | |
|---|---|---|
| Component | Weight Percent | Mass (Grams) |
| DMT (dimenthyl tartrate) | 78 | 148.2 |
| B4G Cyan pigment* | 10 | 19 |
| Solsperse ® 32000 | 10 | 19 |
| Synergist Sunflo ® SFD-B124 | 2 | 3.8 |
| TOTAL | 100.00 | 190 |

*HOSTAPERM ® Blue B4G (commercially available from Clariant)

Comparative Example 14

Comparative ink Example 14 was prepared as follows having the formulation as shown in Table 8. Comparative Example 14 uses a diamide based on 1 equivalent of isophorone diamine and 2 equivalents of mono-acid. The inks of the present disclosure use a monoamine (Amine D) to create mono- and diamides based on 1 equivalent of amine D and 1 equivalent of mono-acid, or 2 equivalents of amine D and 1 equivalent of di-acid, respectively. The present disclosure shows that the Amine D materials surpass the performance of the isophorone diamine based-materials.

TABLE 8

Comparative Example 14

| Component | Weight Percent | Mass (grams) |
|---|---|---|
| distearyl terephthalate | 67.55 | 6.75 |
| Amorphous diamide* | 19.12 | 1.91 |
| Pigment concentrate B4G | 13.33 | 1.33 |
| | 100.00 | 10.00 |

*amorphous diamide of the formula

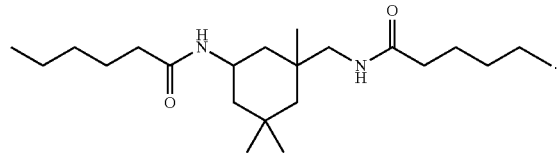 [SMILES: CCCCCC(=O)NCC1(C)CC(NC(=O)CCCCC)CC(C)(C)C1]

Comparative Example 15

Comparative ink Example 15 was prepared as follows having the formulation as shown in Table 9.

TABLE 9

| Component | Weight Percent | Mass (Grams) |
|---|---|---|
| N-phenylethylbenzamide (crystalline)* | 66.7 | 6.67 |
| Sylvatac ™ RE40* (amorphous) | 20 | 2 |
| 15% Pigment dispersion in DST resin (having the components as shown in Table 10) | 13.3 | 1.33 |
| TOTAL | 100.00 | 10 |

*Sylvatac ™ RE40 rosin ester available from Arizona Chemical.
*N-phenylethylbenzamide (crystalline) having the formula

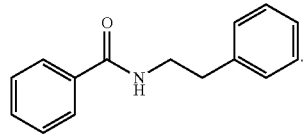 [SMILES: O=C(NCCc1ccccc1)c1ccccc1]

TABLE 10

| Component | Weight Percent | Mass (Grams) |
|---|---|---|
| HOSTAPERM ® Blue B4G | 2 | 0.2 |
| Polyethyleneimine dispersant* | 2 | 0.2 |
| Synergist Sunflo ® SFD-B124 | 0.4 | 0.04 |
| Distearyl Terephthalate (DST, crystalline) | 3.6 | 0.36 |
| Extra DST | 72.88 | |
| Extra DST | | 7.288 |
| Tert-butyl cyclohexyl/cyclohexyl tartrate | 19.12 | |
| Sylvatac ™ RE25** | | 1.91 |
| TOTAL | 100.00 | 10 |

*Polyethyleneimine dispersant prepared as described in Example 1 of U.S. Pat. No. 7,973,186, which is hereby incorporated by reference herein in its entirety.
**Sylvatac ™ RE25 rosin ester available from Arizona Chemical.

Comparative Example 16

Comparative ink Example 16 was prepared as follows having the formulation as shown in Table 11.

TABLE 11

| Component | Weight Percent | Mass (Grams) |
|---|---|---|
| naphthalene 2,6-distearoate (crystalline)* | 76% | 7.7 |
| Tert-butyl cyclohexyl/cyclohexyl tartrate (TBCT PP-TBCT-1) | 10.7 | 1.07 |
| 15% pigment dispersion in TBCT resin | 13.3 | 1.33 |
| TOTAL | 100.00 | 10 |

*naphthalene 2,6-distearoate (crystalline) having the formula

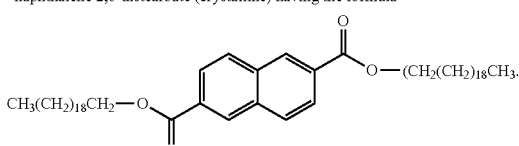

Robustness Tests.

Ink Examples 8, 9, and 10 were printed onto Xerox® Digital Color Elite Gloss, 120 gsm (DCEG) coated papers using the K-proofer gravure printing plate, which is rigged with a pressure roll set at low pressure. The gravure plate temperature was set at 142° C., but the actual plate temperature is about 134° C. The K-proofer apparatus (manufactured by RK Print Coat Instrument Ltd., Litlington, Royston, Heris, SG8 0OZ, U.K.) is a useful printing tool to screen a variety of inks at small scale and to assess image quality on various substrates. The inks gave robust images that could not be easily removed from the substrates. When a metal tip with a curved tip at an angle of about 15° from vertical, with a weight of 528 g applied, was drawn across the image at a rate of approximately 13 mm/s, no ink was visibly removed from the image. The tip is similar to a lathe round nose cutting bit with radius of curvature of approximately 12 mm K-proof samples of ink Examples 8, 9, 10, and Comparative Examples 11, 12, and 14 were made on coated paper (DCEG: Xerox digital Color Elite Gloss, 120 gsm). The K-proofs were spread by feeding each K-proof through a Xerox Phaser® 8400 or Phaser® 8860 printer at 1 inch per second at a drum and paper pre-heat temperature of 50° C. with the ink-surface facing the transfix drum. One K-proof of each ink was then scratched using the XRCC three-finger gouge system, and another K-proof folded along with a Xerox Business 4200 (75 gsm) facing page in a Duplo D-590 folder and evaluated for fold crease. A third K-proof was spread at increasing spreader drum and pre-heat temperatures until offset became apparent (spreader offset can be a limiting factor in what temperature certain print-process steps can be carried out, higher temperatures are better). Fold offset, fold crease, scratch and gloss test results for the K-proof samples of Ink Example 8 and Comparative Examples 11, 12, 13, and 14 are shown in Table 12.

Two K-proofs of each ink spread at 50° C. were visually assessed for scratch and fold crease area. The K-proofs were visually assessed for various robustness metrics including Fold offset, Fold crease, scratch and spread offset. Where a Rank Order was used, the K-proofs were visually compared side-by-side and ranked from best to worst within the set. Table 12 shows K-proof evaluation data for Ink Example 8.

TABLE 12

| Example | Fold Offset Rank Order | Fold Offset SIR Grade | Fold Crease Rank Order | Scratch Rank Order | Gloss 60° (//) |
|---|---|---|---|---|---|
| 8 | 2 | 1.5 | 2 | 2 | 21.5 |
| Comparative Example 11 | 1 | 1 | 1 | 1 | 16.3 |
| Comparative Example 12 | 5 | 2.5 | 5 | 5 | 33.1 |
| Comparative Example 13 | 3 | 2 | 3 | 3 | 24.7 |
| Comparative Example 14 | 4 | 2 | 4 | 4 | 14.8 |
|  | 1 = best 7 = worst | 1 = best 5 = worst | 1 = best 7 = worst | 1 = best 7 = worst | Measured on Spread proof |

TABLE 13

| Example | SIR Grade | SIR Grade | SIR Grade |
|---|---|---|---|
| 9 | 1.5 | 2 | 2 |
| 10 | 1.5 | 2 | 3 |
| Comparative Example 11 | 1 | 1 | 1 |
| Comparative Example 12 | 2.5 | 5 | 5 |
| Comparative Example 13 |  |  |  |
| Comparative Example 15 | 1.5 | 2 | 2 |
| Comparative Example 16 | 2 | 2 | 5 |
|  | 1 = best 5 = worst | 1 = best 5 = worst | 1 = best 5 = worst |

Ink Crystallization Rate (TROM, or Time-Resolved Optical Microscopy).

The ink of Example 8 was tested for rates of crystallization, a measure of speed of solidification. The rate of crystallization was measured by TROM procedure which was described in U.S. patent application Ser. No. 13/456,847, which is hereby incorporated by reference herein in its entirety. The sample was quenched from the melting temperature to 40° C. and the crystallization process was followed by Polarized Optical Microscopy. Table 14 summarizes the TROM results for ink Example 8.

TABLE 14

| Example | Ttest (° C.) | Time Crystallization Onset (seconds) | Time Crystallization Elapsed (seconds) | Time Crystallization Total (seconds) |
|---|---|---|---|---|
| 8 | 140 | 4 | 1 | 5 |

In embodiments, an amorphous monoamide compound based on Amine D is provided. In other embodiments, an amorphous diamide compound based on Amine D is provided. It is believed that the present compounds provided the first example of amide materials having a suitable viscosity for amorphous materials which enable use in certain applications such as phase change or solid ink applications. In embodiments, the amorphous monoamides and amorphous diamides described herein demonstrated superior robustness over previous phase change ink materials. In certain embodiments, the amorphous compounds herein are derived from bio-renewable feedstocks.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

The invention claimed is:

1. A compound of the formula

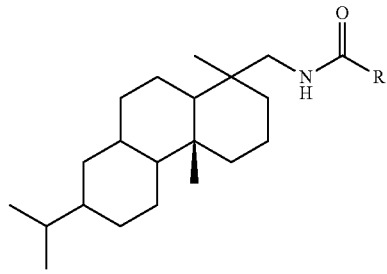

wherein R is selected from the group consisting of an alkyl group, an aryl group, an alkylaryl group, an arylalkyl group, and combinations thereof.

2. The compound of claim 1, wherein R is an alkyl group having from about 1 to about 22 carbon atoms.

3. The compound of claim 1, wherein R is an alkyl group having from about 2 to about 18 carbon atoms.

4. The compound of claim 1, having the formula

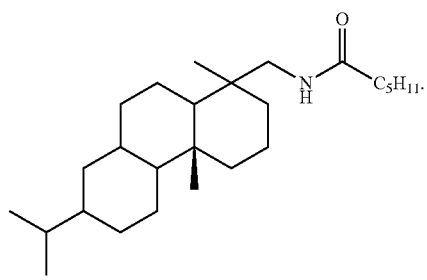

5. The compound of claim 1, having the formula

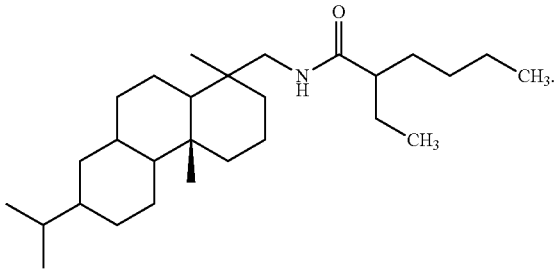 [SMILES: CCCCC(CC)C(=O)NCC1(C)CCC[C@]2(C)C3CCC(C(C)C)CC3CCC12]

6. The compound of claim 1, having the formula

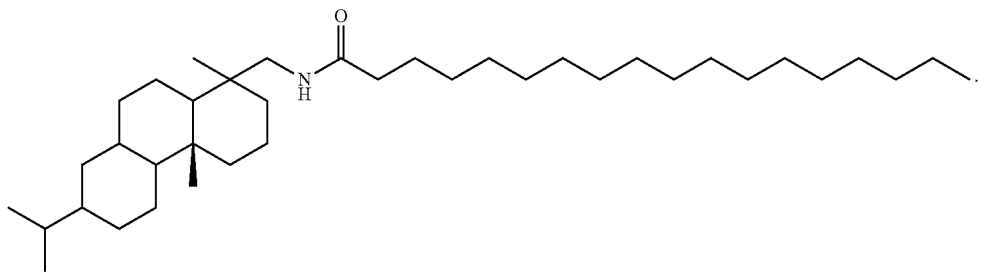 [SMILES: CCCCCCCCCCCCCCCCCC(=O)NCC1(C)CCC[C@]2(C)C3CCC(C(C)C)CC3CCC12]

7. A method for preparing an amorphous monoamide comprising:

contacting a compound of the formula

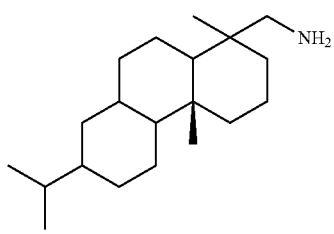 [SMILES: CC(C)C1CCC2C(CCC3C(C)(CN)CCC[C@]23C)C1]

with an acid of the formula

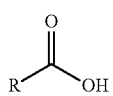

with mixing and optional heating to produce a product compound of the formula

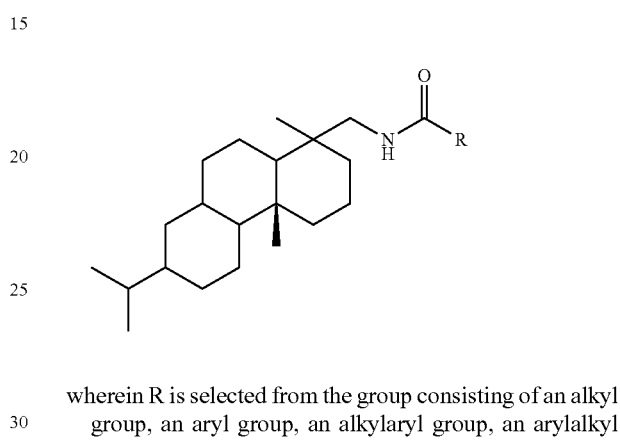

wherein R is selected from the group consisting of an alkyl group, an aryl group, an alkylaryl group, an arylalkyl group, and combinations thereof.

8. The method of claim 7, further comprising a catalyst.

9. The method of claim 7, wherein heating comprises heating to a temperature of from about 160 to about 180° C.

10. The method of claim 7, further comprising applying a vacuum pressure of from about 1 to about 2 millimeters of mercury for a period of from about 1 minute to about 1 hour.

11. The method of claim 7, wherein the product compound is of the formula

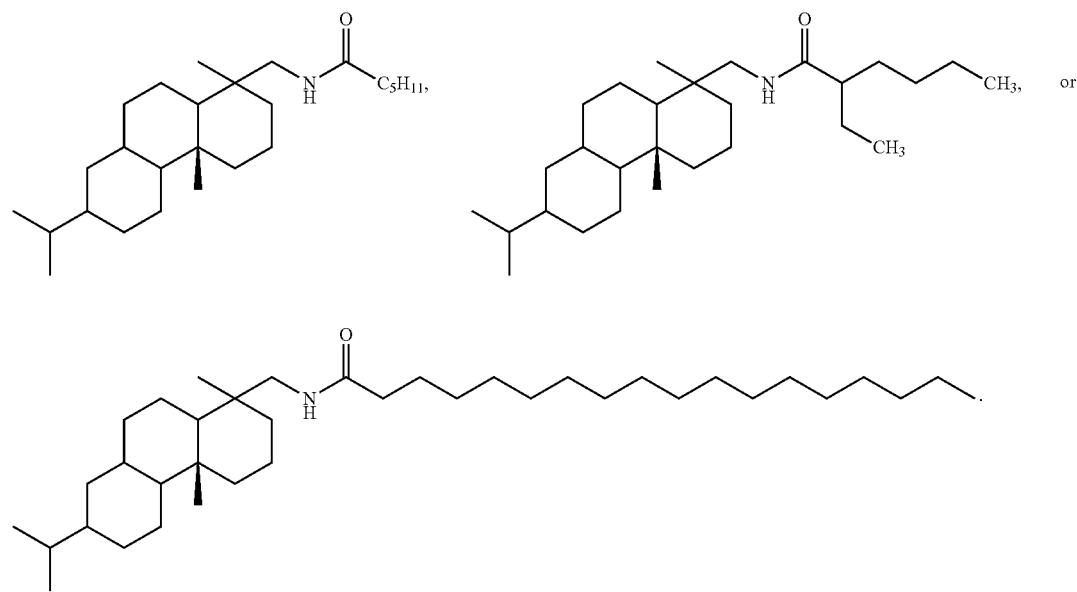

* * * * *